(12) United States Patent
Miller

(10) Patent No.: US 9,668,840 B2
(45) Date of Patent: Jun. 6, 2017

(54) ORAL HYGIENE APPLIANCE WITH BRISTLE CHARACTERISTICS FOR EFFECTIVE CLEANING

(75) Inventor: Kevin A Miller, Bellevue, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 852 days.

(21) Appl. No.: 13/993,092

(22) PCT Filed: Dec. 20, 2011

(86) PCT No.: PCT/IB2011/055801
§ 371 (c)(1),
(2), (4) Date: Aug. 26, 2013

(87) PCT Pub. No.: WO2012/085832
PCT Pub. Date: Jun. 28, 2012

(65) Prior Publication Data
US 2013/0333126 A1    Dec. 19, 2013

Related U.S. Application Data

(60) Provisional application No. 61/424,718, filed on Dec. 20, 2010.

(51) Int. Cl.
*A61C 17/22* (2006.01)
*A46B 9/02* (2006.01)
*A46B 9/04* (2006.01)

(52) U.S. Cl.
CPC ............ *A61C 17/222* (2013.01); *A46B 9/026* (2013.01); *A46B 9/04* (2013.01); *A46B 9/045* (2013.01)

(58) Field of Classification Search
CPC ......... A61C 17/222; A46B 9/026; A46B 9/04; A46B 9/045
See application file for complete search history.

(56) References Cited

U.S. PATENT DOCUMENTS

| 4,237,574 | A | | 12/1980 | Kelly et al. | |
|---|---|---|---|---|---|
| 4,428,659 | A | * | 1/1984 | Howard | G03F 7/305 118/304 |
| 5,396,678 | A | * | 3/1995 | Bredall | A46B 9/04 15/167.1 |

(Continued)

FOREIGN PATENT DOCUMENTS

| DE | 19533144 A1 | 3/1997 |
|---|---|---|
| JP | 05508566 A | 12/1993 |

(Continued)

OTHER PUBLICATIONS

Pretara-Spanedda et al: "Toothbrush Bristle Density: Relationship to Plaque Removal"; Am. J. Dent., 1989, 2(6), pp. 345-348.

*Primary Examiner* — Robert Scruggs

(57) ABSTRACT

An oral cleaning appliance, such as a toothbrush (10) or a mouthpiece (20), includes a bristle arrangement which comprises a base member and a field of bristles for contacting and cleaning teeth, wherein the bristle field (17, 26) has bristles with a density of between 2-7%, and wherein the individual bristle filaments have a stiffness characterized by a deflection of no greater than 50% of their length for a bristle tip pressure of 6 Newtons/cm$^2$ and a deflection reaching 50% for a bristle tip pressure of 85 Newtons/cm$^2$.

11 Claims, 4 Drawing Sheets

(56) References Cited

U.S. PATENT DOCUMENTS

| | | | |
|---|---|---|---|
| 6,021,541 A | 2/2000 | Mori et al. | |
| 6,321,407 B1 | 11/2001 | Weihrauch | |
| 2003/0221272 A1 | 12/2003 | Lehman | |
| 2004/0128777 A1* | 7/2004 | Koh | A46B 9/045 15/22.1 |
| 2007/0067933 A1 | 3/2007 | Waguespack | |
| 2009/0255077 A1 | 10/2009 | Mori et al. | |
| 2010/0024142 A1* | 2/2010 | Townley | A46B 9/026 15/167.1 |
| 2011/0252590 A1* | 10/2011 | Steur | A61C 17/16 15/167.2 |

FOREIGN PATENT DOCUMENTS

| | | |
|---|---|---|
| JP | 09322821 A | 12/1997 |
| JP | 2003009949 A | 1/2003 |
| JP | 2006068473 A | 3/2006 |
| JP | 2007151704 A | 6/2007 |
| JP | 2008036098 A | 2/2008 |
| KR | 20080095011 A | 10/2008 |
| WO | 9119437 A1 | 12/1991 |
| WO | 2007112112 A1 | 10/2007 |
| WO | 2007122112 A1 | 11/2007 |
| WO | 2009150559 A1 | 12/2009 |
| WO | 2011077283 A1 | 6/2011 |

* cited by examiner

ORAL HYGIENE APPLIANCE WITH BRISTLE CHARACTERISTICS FOR EFFECTIVE CLEANING

This invention relates generally to teeth cleaning appliances such as toothbrushes and mouthpieces, and more specifically concerns the arrangement of bristles on the appliance.

In order to produce effective teeth cleaning with a bristle field, either as part of a brush member of a toothbrush or a mouthpiece teeth cleaning appliance, it is important to maintain at least a threshold level of bristle tip pressure against the teeth. It has been found, particularly with user operated toothbrushes, either manual or power, that a user typically does not apply sufficient force, i.e. sufficient load, against the teeth in order to produce the necessary level of bristle tip pressure for effective cleaning. Typically, the bristle tip pressure is sufficient to eliminate just 40%, i.e. the top portion, of plaque on the teeth. The remaining portion of the plaque, i.e. that portion closest to the tooth surface, is more tenacious and requires a greater bristle tip pressure to remove than is typically applied. It is, however, quite desirable to remove this remaining portion of plaque for effective teeth cleaning and resulting good dental health.

Accordingly, it is desirable that effective bristle tip pressures be produced with the use of reasonable average force by the user. A bristle field with particular characteristics helps to achieve the desired bristle tip pressure for effective cleaning with a reasonable force/load applied by the user, without resulting discomfort to the user.

Accordingly, disclosed herein is an oral teeth cleaning appliance, comprising: a handle; and a brushhead assembly extending from the handle, the brushhead assembly including a brushhead member which comprises a base member and a field of bristles for contacting and cleaning teeth, wherein the bristle field has a bristle density in the range of 2-7%, and wherein the individual bristle filaments have a stiffness characterized by a bristle deflection of not greater than 50% of their length with a bristle tip pressure of 6 Newtons/cm$^2$, thereby effectively supporting a bristle tip pressure within the range for effective cleaning.

Figures 1, 2:
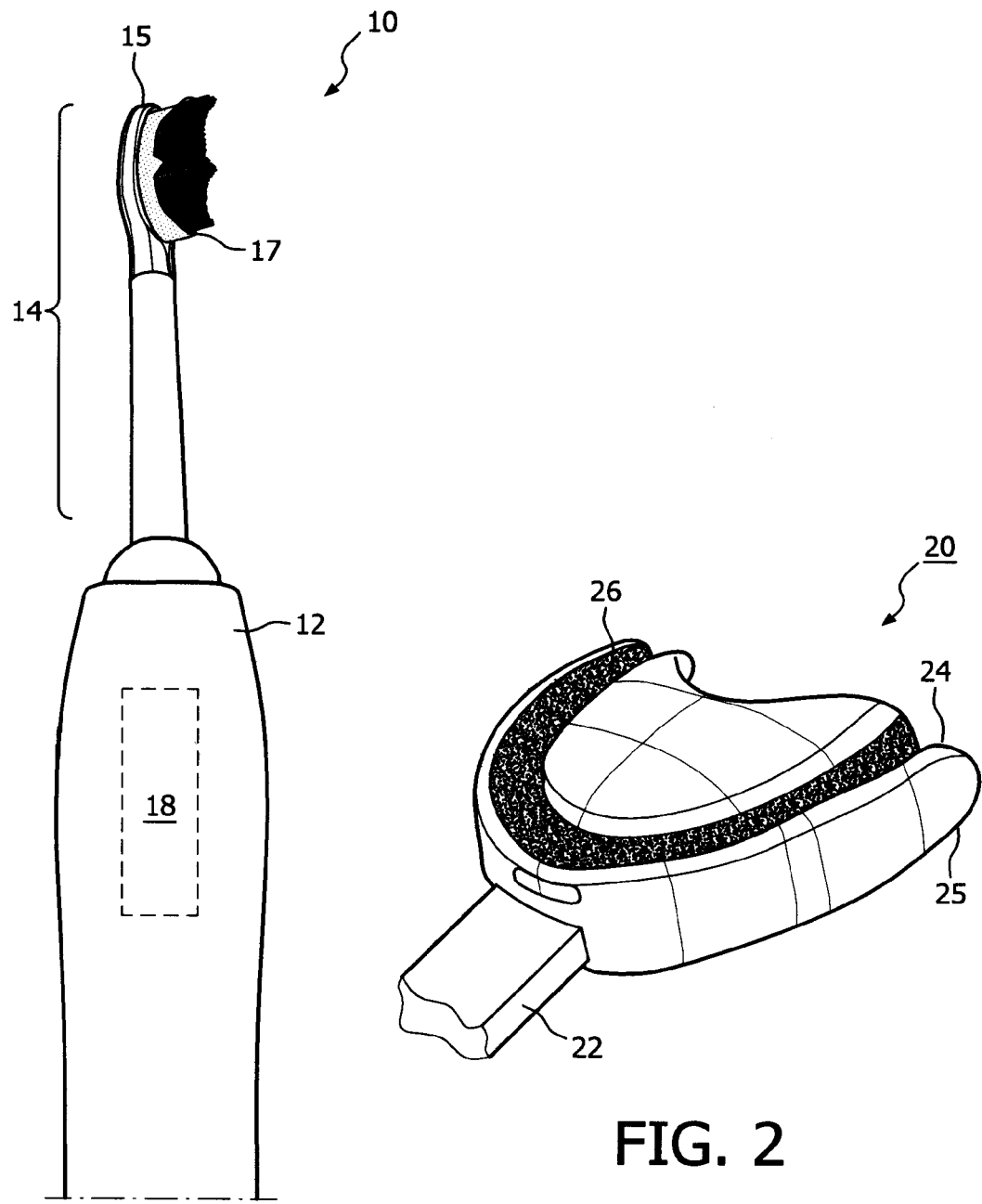
FIGS. 1 and 2 show top views of two bristle field arrangements, one for a toothbrush and one for a mouthpiece.

FIG. 1 shows a toothbrush generally at 10 which includes a handle portion 12 and a brushhead assembly 14, the brushhead assembly including a brush member with a bristle base plate 15 and a bristle field 17. The toothbrush 10 could either be a manual toothbrush or a power toothbrush, with a drive system referred to at 18 which drives the brushhead assembly and the bristle field in a selected motion, such as rotationally back and forth through a selected angle, e.g. 11° or other effective angle, such as in the range of 9-20°.

FIG. 2 shows in general a dental cleaning mouthpiece 20 with a drive assembly 22. The drive assembly 22 could be located in a part which extends away from the mouthpiece as shown, or part of the mouthpiece itself for hands-free operation. The mouthpiece could include upper and lower tray sections 24, 25 to accommodate the upper and lower jaws, or a single tray for just one of the jaws. Attached or imbedded into the surface of the trays is a bristle field shown generally at 26 for cleaning of teeth.

The present invention is directed toward the physical characteristics of a bristle field, as part of a brush member portion of a brushhead assembly for a toothbrush, whether manual or power, or as part of a bristle assembly portion of a mouthpiece, which increases the cleaning effectiveness of the appliance by supporting an increased value of bristle tip pressure for a given force applied by the user. In particular, as an example, for those toothbrushes which have an average user load of 100 grams, the bristle field described and shown herein includes particular values of bristle density and bristle stiffness which result in an increased value of bristle tip pressure which in turn is effective to significantly improve cleaning. These values of bristle density and stiffness are said to support effective levels of bristle tip pressure with average levels of force applied by a user. The use of a conventional high bristle density and insufficient stiffness would otherwise result in insufficient bristle tip pressure for effective cleaning with average user force, in one example, 100 grams.

Figure 7:
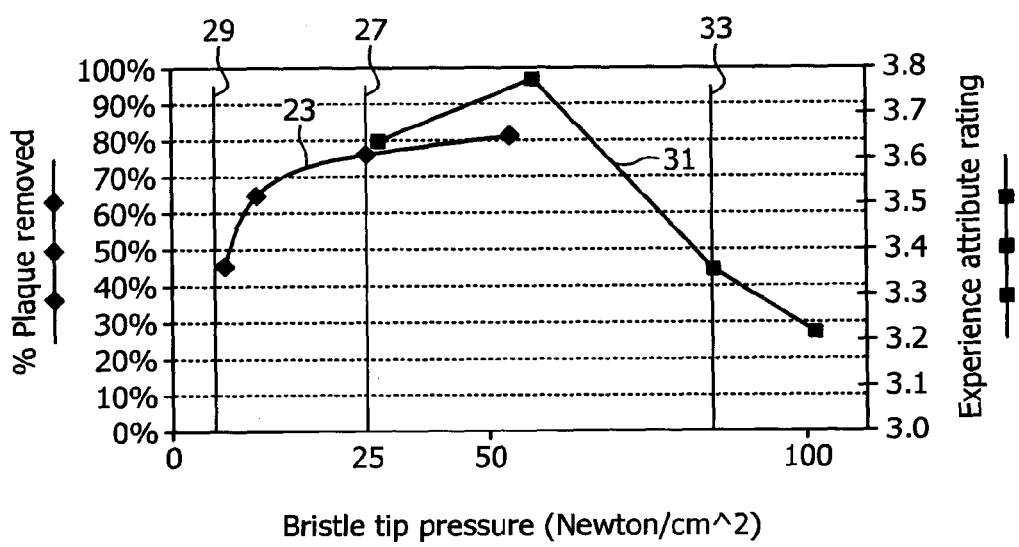
FIG. 7 is a graph of bristle tip pressure against percent of plaque removed and comfort rating.

As indicated above, a sufficient level of bristle tip pressure is necessary to achieve effective cleaning, by removing a significant portion of tenacious plaque. Bristle density and bristle stiffness are important factors in supporting a bristle tip pressure sufficient to produce the desired cleaning, without the necessity of extreme force values. FIG. 7 is a graph showing the increase in plaque removal on one axis relative to bristle tip pressure (line 23), to comfort (user experience) on the other axis relative to bristle tip pressure (line 31). The graph shows that above a value of 25 Newtons/cm$^2$ at 27, plaque removal does not increase significantly with additional bristle tip pressure. A typical value of bristle tip pressure for existing conventional user-loaded toothbrushes (100 grams in the example) with a conventional bristle field, is 6 Newtons/cm$^2$, referred to at 29 on the graph. At a bristle tip pressure of 85 Newton/cm$^2$ at 33, discomfort becomes significant.

Figure 3:
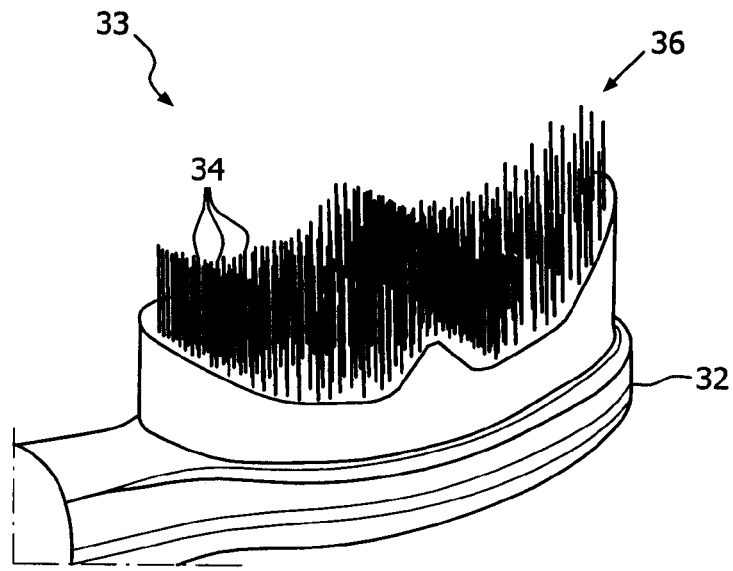
FIG. 3 is a close-up view of a bristle field of a toothbrush using single filament.
Figure 8:
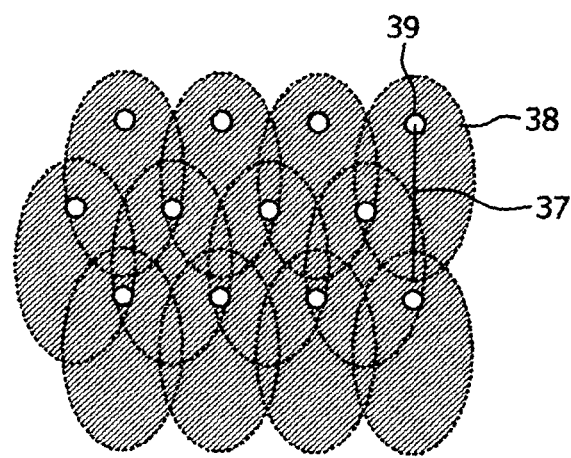
FIG. 8 is a diagram showing overlapping coverage of individual bristle filaments in a bristle field.

FIG. 3 shows one embodiment of a brush member 33 which is part of a brushhead assembly for use in a toothbrush and which has a bristle field with the desired characteristics of bristle density and stiffness to support effective bristle pressure. The brush member 31 includes a bristle base plate 32 to which are attached or mounted a plurality of individual bristle filaments 34-34 comprising the bristle field 36. The first characteristic of the present bristle field is bristle density. The total cross-sectional area of the individual filaments divided by the area of coverage of the entire bristle field defines bristle density. In the present embodiment, the bristle density is between 2% and 7%, preferably between 2% and 3%. This value of bristle density is substantially lower than the bristle density of conventional bristle fields used for oral cleaning. Typically, the individual filaments in the present bristle field arrangement will be equally spaced over the area of the bristle field to give good overall cleaning coverage in accordance with the stroke 37 of the individual bristles 39, which typically is about 1 mm for a typical bristle filament. Usually, some overlap of coverage 38 of each bristle 39 will produce a good overall cleaning effect, as shown in FIG. 8.

Figure 4:
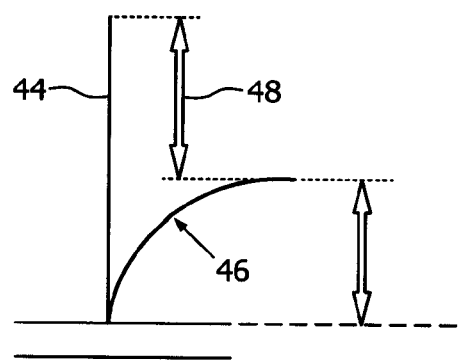
FIG. 4 is an elevational view showing the maximum deflection of a single filament upon application of a particular level of force/load.

The other significant characteristic of the present bristle field is the stiffness of the individual bristle filaments. Referring to FIG. 4, the bristle stiffness in the embodiment shown is such that it will support a bristle tip pressure of 6 Newtons/cm$^2$ grams without the bristle deflecting more than 50% of the overall length of the bristle. In one example, the pressure value will be accomplished with a force of 100 grams and a brush member bristle field disclosed herein. Deflection is shown in FIG. 4. The undeflected bristle is shown at 44, while the deflected bristle is shown at 46. The 50% deflection value is shown at 48. This is the minimum value of bristle stiffness for the bristles in the bristle field, i.e. for a bristle tip pressure of 6 Newtons/cm$^2$, the bristles will not deflect any more than 50% of their length. If the bristle deflects more than 50% at this value of bristle tip pressure, it is too soft for effective cleaning, as they will lay over and not produce the contact required for effective cleaning and performance becomes non-linear. For the maximum value of bristle stiffness, the bristles must deflect 50% of their length (no less) at an applied bristle tip pressure of 85 Newtons/cm$^2$, i.e. when applied bristle tip pressure reaches 85 Newtons/cm$^2$, the bristles will deflect at least 50% of their length. If the bristles do not deflect 50% of their length as bristle tip pressure reaches 85 Newtons/cm$^2$, the bristles are too stiff and produce discomfort. A stiffness value lower than the minimum will not produce the desired cleaning effect, while a value higher than the maximum will produce discomfort to the user.

Figure 6:
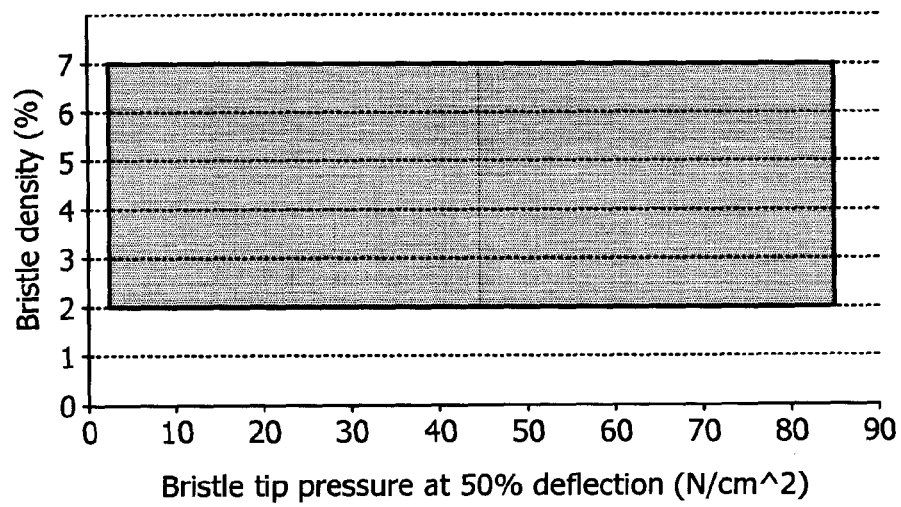
FIG. 6 is a graph showing the desired area of bristle tip pressure versus bristle density.

FIG. 6 shows a graph with bristle density along one axis and bristle stiffness along the other orthogonal axis. The area 50 defined by bristle density of between 2-7% on the one axis and a bristle stiffness represented by 50% deflection of the bristles between bristle tip pressures of 6 and 85 Newtons/cm$^2$ on the other axis represents the operating area for effective cleaning, without causing discomfort to the user.

Another characteristic of an effective bristle field is the physical profile of the bristle field, i.e. the geometry of the tips of the bristles in the bristle field, referred to as profile trim. The bristle profile can, however, vary, although preferably it is not flat.

Figure 5:
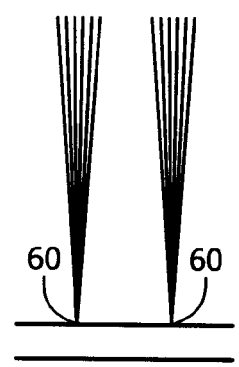
FIG. 5 is an elevational view of a bristle field with tufts comprising a small number of filaments.

Although FIG. 1 shows an embodiment using evenly spaced individual filaments, small bristle tufts could also be used, as shown in FIG. 5. Typically, in the present embodiment, if tufts are used rather than individual filaments, a tuft should not have any more than six filaments. A single such filament is shown at 60 in FIG. 5. The small number of filaments allows the tufts to splay out to some extend in use, yet remain effective in cleaning and support the desired higher bristle tip pressures. Again, the individual tufts should be spaced evenly to provide good overall coverage, preferably somewhat overlapping, in operation.

Although the bristle field is described in detail with respect to a brushhead embodiment, similar bristle field characteristics apply to the bristle field in the mouthpiece embodiment, specifically the bristle density and bristle stiffness characteristics.

The above bristle field characteristics, specifically bristle density, bristle stiffness and profile trim will support increased bristle tip pressure for a given load for increased efficacy of plaque removal with uniform coverage. This includes reducing or eliminating the more tenacious plaque which is missed by the action of most manual and dental appliances using average user applied load.

Although a preferred embodiment has been disclosed for purposes of illustration, it should be understood that various changes and modifications and substitutions could be made in the preferred embodiment without departing from the spirit of the invention as defined by the claims which follow:

The invention claimed is:

1. An oral teeth cleaning appliance, comprising:
   a handle; and
   a brushhead assembly extending from the handle, the brushhead assembly including a brush member which comprises a base member and a field of bristles for contacting and cleaning teeth, wherein the bristle field has a bristle density in the range of 2-7%, and wherein the individual bristle filaments have a stiffness characterized by a bristle deflection of not greater than 50% of their length when a bristle tip pressure of 6 Newtons/cm$^2$ is applied, and wherein the individual bristle filaments have a bristle stiffness characterized by a bristle deflection of at least 50% of their length when a bristle tip pressure of 85 Newtons/cm$^2$ is applied, thereby effectively supporting effective cleaning and removal of plaque.

2. The oral cleaning appliance of claim 1, wherein the bristle density is in the range of 2-3%.

3. The oral cleaning appliance of claim 1, wherein the appliance is a manual toothbrush.

4. The oral cleaning appliance of claim 1, wherein the appliance is a power toothbrush.

5. The oral cleaning appliance of claim 1, wherein the bristle field has a profile other than flat.

6. The oral cleaning appliance of claim 1, wherein the bristle field comprises individual bristle filaments substantially evenly spaced over the bristle field and positioned so as to provide some overlap in coverage on the teeth during operation of the appliance.

7. The oral cleaning appliance of claim 1, wherein the bristles field comprises a plurality of bristle tufts, with no more than 6 individual bristle filaments per tuft, the bristle tufts spaced substantially evenly over the bristle field and positioned so as to provide some overlap in coverage on the teeth during operation of the appliance.

8. An oral cleaning appliance, comprising:
   a mouthpiece having one or more trays to accommodate the teeth of a user;
   a drive assembly for the mouthpiece; and
   a bristle field positioned in at least one of the trays, comprising a set of bristles attached to the trays for contacting and cleaning teeth in operation of the mouthpiece, wherein the bristle field has a bristle density of 2-7% and wherein the individual bristles have a stiffness characterized by a deflection of not greater than 50% of their length when a bristle tip pressure 6 Newtons/cm$^2$ is applied, and wherein the individual bristle filaments have a bristle stiffness characterized by a bristle deflection of at least 50% of their length when a bristle tip pressure of 85 Newtons/cm$^2$ is applied, effectively supporting effective cleaning and removal of plaque.

9. The oral cleaning appliance of claim 8, wherein the bristle density is in the range of 2-3%.

10. The oral cleaning appliance of claim 8, wherein the bristle field comprises individual bristle filaments, substantially evenly spaced over the bristle field and positioned so as to overlap in coverage on the teeth during operation of the appliance.

11. The oral cleaning appliance of claim 8, wherein the bristle field comprises a plurality of tufts, with no more than 6 bristle filaments per tuft, the individual tufts being substantially evenly spaced over the bristle field and positioned to provide overlap in coverage on the teeth during operation of the appliance.

* * * * *